US010335961B2

(12) United States Patent
Christiansen et al.

(10) Patent No.: US 10,335,961 B2
(45) Date of Patent: Jul. 2, 2019

(54) SUPPORT ARM SYSTEM WITH AT LEAST ONE LOCKABLE ARTICULATED CONNECTION AND METHOD FOR OPERATING SUCH A SUPPORT ARM SYSTEM

(71) Applicant: Drägerwerk AG & Co. KGaA, Luebeck (DE)

(72) Inventors: Nils Christiansen, Luebeck (DE); Dhafir Jader, Ratzeburg (DE); Stanislav Askulskij, Luebeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 119 days.

(21) Appl. No.: 15/593,401

(22) Filed: May 12, 2017

(65) Prior Publication Data
US 2017/0326738 A1    Nov. 16, 2017

(30) Foreign Application Priority Data

May 13, 2016    (DE) .......................... 10 2016 005 785

(51) Int. Cl.
*F16M 11/08* (2006.01)
*B25J 19/00* (2006.01)
(Continued)

(52) U.S. Cl.
CPC .......... *B25J 19/0004* (2013.01); *A61B 34/30* (2016.02); *A61B 34/70* (2016.02); *A61B 90/50* (2016.02); *B25J 9/161* (2013.01); *B25J 9/1674* (2013.01); *B25J 13/00* (2013.01); *B25J 17/00* (2013.01); *F16C 11/10* (2013.01); *F16D 49/08* (2013.01); *F16D 49/16* (2013.01); *F16D 65/16* (2013.01); *F16M 11/08* (2013.01); *F16M 13/02* (2013.01); *A61B 2034/305* (2016.02); *A61B 2090/508* (2016.02); *F16C 11/103* (2013.01); *F16D 2121/22* (2013.01); *F16M 2200/022* (2013.01); *F16M 2200/024* (2013.01); *F16M 2200/06* (2013.01); *Y10S 901/09* (2013.01); *Y10S 901/20* (2013.01)

(58) Field of Classification Search
USPC ...................................... 248/274.1
See application file for complete search history.

(56) References Cited

U.S. PATENT DOCUMENTS 4,943,296 A * 7/1990 Funakubo ............... A61F 9/013
606/166
5,337,878 A * 8/1994 Mehlert .................. B66D 5/08
188/171

(Continued)

FOREIGN PATENT DOCUMENTS

DE    297 18 548 U1    3/1998
DE    694 19 124 T2    1/2000
(Continued)

Primary Examiner — Monica E Millner
(74) Attorney, Agent, or Firm — McGlew and Tuttle, P.C.

(57) ABSTRACT

A support arm system (10) has at least one lockable articulated connection (16). A locking device (20) is associated with the articulated connection (16). The locking device (20) includes a passive drive (32) as well as an actuating device (36) associated with the locking device (20) with an active drive (38). The active drive (38) acts in the same plane as the passive drive (32).

20 Claims, 5 Drawing Sheets

(51) Int. Cl.

| | | |
|---|---|---|
| *A61B 34/30* | (2016.01) | |
| *A61B 34/00* | (2016.01) | |
| *B25J 9/16* | (2006.01) | |
| *B25J 13/00* | (2006.01) | |
| *B25J 17/00* | (2006.01) | |
| *F16C 11/10* | (2006.01) | |
| *F16D 49/08* | (2006.01) | |
| *F16D 65/16* | (2006.01) | |
| *F16M 13/02* | (2006.01) | |
| *F16D 49/16* | (2006.01) | |
| *A61B 90/50* | (2016.01) | |
| *F16D 121/22* | (2012.01) | |

(56) References Cited

U.S. PATENT DOCUMENTS

| | | | | |
|---|---|---|---|---|
| 5,494,034 | A * | 2/1996 | Schlondorff | A61B 6/501 |
| | | | | 378/20 |
| 6,095,468 | A * | 8/2000 | Chirico | F16M 11/2014 |
| | | | | 248/125.7 |
| 6,324,934 | B1 * | 12/2001 | Monaghan | B25J 9/042 |
| | | | | 74/490.04 |
| 6,817,585 | B2 * | 11/2004 | Wagner | F16M 11/10 |
| | | | | 248/324 |
| 7,411,576 | B2 * | 8/2008 | Massie | G06F 1/206 |
| | | | | 345/156 |
| 7,770,860 | B1 | 8/2010 | Culpepper et al. | |
| 8,141,188 | B2 * | 3/2012 | Lubbers | F16D 63/008 |
| | | | | 5/658 |
| 8,254,092 | B2 * | 8/2012 | Russell | F16M 11/08 |
| | | | | 248/125.7 |
| 8,834,488 | B2 * | 9/2014 | Farritor | A61B 1/00158 |
| | | | | 606/130 |
| 9,400,503 | B2 * | 7/2016 | Kearns | B25J 11/009 |
| 9,999,480 | B2 * | 6/2018 | Oginski | A61G 12/002 |
| 2011/0303499 | A1 | 12/2011 | Chandan et al. | |
| 2015/0366336 | A1 | 12/2015 | Wong | |
| 2017/0156808 | A1 * | 6/2017 | Auld | A61B 34/77 |

FOREIGN PATENT DOCUMENTS

| | | |
|---|---|---|
| DE | 10 2014 002 733 A1 | 9/2014 |
| DE | 10 2014 114 477 B3 | 2/2016 |

* cited by examiner

SUPPORT ARM SYSTEM WITH AT LEAST ONE LOCKABLE ARTICULATED CONNECTION AND METHOD FOR OPERATING SUCH A SUPPORT ARM SYSTEM

CROSS REFERENCE TO RELATED APPLICATIONS

This application claims the benefit of priority under 35 U.S.C. § 119 of German Application 10 2016 005 785.8, filed May 13, 2016, the entire contents of which are incorporated herein by reference.

FIELD OF THE INVENTION

The present invention pertains to a support arm system with at least one lockable articulated connection and further to a method for operating such a support arm system.

BACKGROUND OF THE INVENTION

Support arm systems are known per se. In case of a medical application, a support arm system is used, for example, for the flexible positioning of a medical device or the like in the room. The support arm system comprises for this at least one articulated connection, namely, an articulated connection in the form of a rotary hinge. Depending on a concrete embodiment and a particular application, the support arm system may have a plurality of such hinges. The support arm system has at least one rotary hinge either between an extension arm, which is fastened, for example, to a wall of a building and is oriented horizontally or essentially horizontally, as well as an arm segment or between a support, which projects upwards from a floor surface or is arranged suspended on a room ceiling and is oriented vertically or essentially vertically, as well as an arm segment. Because of the articulated arrangement on an extension arm, a support or the like, hereinafter called basic segment for short, the arm segment is pivotably movable in a horizontal or at least essentially horizontal plane relative to the basic segment. Additional, likewise movable arm segments, which are connected in an articulated manner to the respective arm segment located in front of them along a kinematic chain thus resulting, may adjoin the movable arm segment.

Such a support arm system is basically known from US 2011/303499 A1. Lockability of the articulated connection between a basic segment and an arm segment adjoining it is also already known from this document.

A defined position of a medical device being carried by the support arm system in the room can be fixed by means of such a lockability. The locking is released and the at least one arm segment of the support arm system is re-oriented to change this position. The locking is then activated again and the support arm system is fixed in the resulting new configuration.

SUMMARY OF THE INVENTION

Based on the device known from US 2011/303499 A1 for locking an articulated connection of a support arm system, one object of the present invention is to provide an additional embodiment of a support arm system with at least one lockable articulated connection, especially such an embodiment in which the lockability of the articulated connection has a comparatively simple configuration and which can accordingly be manufactured at a low cost and requires little maintenance during the operation.

This object is accomplished according to the present invention by means of a support arm system. Provisions are made for this in a support arm system with at least one lockable articulated connection (hinge), wherein a locking device with a passive drive is associated with the articulated connection and wherein an actuating device with an active drive is associated with the locking device, for the active drive to act on the locking device, especially on a brake shoe lever comprised by the locking device, in the same plane as the passive drive.

The advantage of the support arm system being proposed here is that the active drive acting in the same plane as the passive drive represents an especially simple and maintenance-friendly embodiment of an actuating device. The actuating device only requires a few parts, it is thus comparatively inexpensive and can have a compact configuration.

In US 2011/303499 A1 mentioned in the introduction, the tension spring acting as a passive drive there acts in a first plane, while the active drive for electromagnetically moving a plunger intended for releasing the locking acts in a plane perpendicular thereto. Not only a special shape of the plunger, but also mediatingly acting balls between the plunger and the brake shoes are necessary for diverting the direction in which the force acts.

Another advantage of the support arm system proposed is that compressed air is not necessary either for locking the articulated connection nor for releasing the locking. Compressed-air brakes acting as a locking device are known, but they inevitably require the availability of compressed air. Since compressed air cannot be assumed to be generally available even in a medical environment, the independence of the support arm system being proposed here from compressed air is an advantage.

Advantageous embodiments of the present invention are the subject of the subclaims. References used in this connection indicate the further perfection of the subject of the principal claim by the features of the respective subclaim and shall not be construed as representing an abandonment of achieving an independent material protection for the combinations of the features of the related subclaims. Furthermore, it shall be assumed in respect to an interpretation of the claims in case of a more specific concretization of a feature in a subclaim that such a limitation is not present in the respective preceding claims. Finally, it should be noted that the support arm system may also be perfected according to the features of the method for the application of which it may be perfected, especially such that the support arm system comprises means for carrying out the respective embodiment of the method and of the method steps comprised thereby. The method for operating the support arm system may likewise be perfected corresponding to the functionality of the material aspects of the support arm system.

In one embodiment of the support arm system, the locking device comprises at least one brake shoe lever, especially two brake shoe levers, wherein the active drive acts directly on the at least one brake shoe lever. An embodiment in which the active drive or each drive acts directly on the at least one brake shoe lever avoids otherwise necessary intermediate pieces acting in a mediating (force-transmitting) manner, for example, balls, as they are provided in US 2011/303499 A1, which cause the active drive to act only indirectly on the brake shoes.

In a special embodiment of the support arm system, the active drive and the passive drive of the actuating device act not only in the same plane, but also along a common axis on the locking device, especially on the at least one brake shoe lever comprised thereby. The action of the active drive and of the passive drive in the same plane concentrates the components comprised thereby in this plane and around this plane. The action along a common axis additionally concentrates these components in the area of this axis. An even more compact mode of construction will result in this manner.

In another embodiment of the support arm system, at least one electromagnet associated with a free end of a brake shoe lever acts as an active drive. The respective brake shoe lever is correspondingly manufactured from a ferromagnetic material or is provided with a ferromagnetic material at its free end, for example, in the form of a core of the electromagnet, which core is arranged on the brake shoe lever and is movable axially to a coil of the electromagnet. In the energized state, an electromagnet is known to generate a magnetic field. The free end of the brake shoe lever, which end is located opposite the side that is articulated in a pivotably movable manner, is pivoted based on the action of the magnetic field, and the pivoting causes an otherwise given braking effect, which locks the articulated connection, being gradually eliminated and finally eliminated altogether. An electric motor, which drives a spindle mechanism acting at the free end of the brake shoe lever or meshes with a toothed rack meshing with the free end of the brake shoe lever by means of a driven pinion, may also be considered for use as an active drive as an alternative.

In yet another embodiment of the support arm system, two electromagnets act as the active drive, said electromagnets being associated together with a locking device and each electromagnet being associated with one of the two brake shoe levers of the locking device. Each of the two brake shoe levers of a lockable articulated connection can be deflected in such an embodiment by means of an electromagnet to eliminate the otherwise resulting braking effect. Aside from the pivotably movable brake shoe levers themselves, no movable parts are needed for the locking device. In particular, no movable parts are needed, either, as they would otherwise be needed in case of only one electromagnet in order to transmit, for example, a pivoting motion of one of the two brake shoe levers, which motion is induced by means of the electromagnet, to the respective other brake shoe lever as well.

In another special embodiment of the support arm system, at least one compression spring associated with a free end of a brake shoe lever acts as a passive drive. A compression spring is characterized by a comparatively strong spring force with a very small size. The use of a compression spring as a passive drive for bringing about the braking effect by actuating the brake shoe lever—or optionally of two compression springs for actuating a respective brake shoe lever each—consequently leads to an even more compact design of the actuating device of the locking device.

In yet another embodiment of the support arm system, a compression spring acting as a passive drive concentrically surrounds, in at least some sections, a core of an electromagnet acting as an active drive. This coaxial arrangement of the compression spring and of the core of the electromagnet is an example of an embodiment in which the active drive and the passive drive of the actuating device act on the locking device, especially on the at least one brake shoe lever comprised thereby, not only in the same plane but also along a common axis. The compression spring concentrically surrounding the core does not lead to an increase in the size of the actuating device if the compression spring is, for example, in contact with a front side of the electromagnet on one side and acts indirectly or directly on the free end of the brake shoe lever on the opposite side.

Finally, provisions are made in a special embodiment of the support arm system for the locking device to have two brake shoe levers with brake linings facing one another, wherein one active drive each acts directly on one of the two brake shoe levers. Compared to an individual brake shoe lever, two brake shoe levers lead to an increased braking effect and hence to an even better locking of the articulated connection. Due to one active drive, especially one active drive and one passive drive each acting on a brake shoe lever, each brake shoe lever can be actuated individually for establishing and eliminating the braking effect. An active drive associated with each brake shoe lever avoids a deflection mechanism or the like, as it would be necessary if a single active drive acted directly on a brake shoe lever and, by means of the deflection mechanism, indirectly on the other brake shoe lever.

In a method for operating a support arm system of the type here and hereinafter described, a control signal is generated for actuating a circuit component upon an actuation of an operating element, and the active drive of the actuating device is activated by means of the circuit component. A user of the support arm system can consequently deactivate the locking of the articulated connection or one of a plurality of articulated connections of the support arm system by means of the operating element.

In one embodiment of the method, an input signal, which is processed by a control unit and which generates the control signal or at least one control signal for actuating a circuit component upon the input signal, is generated upon an actuation of the operating element. The use of a control unit processing the input signal and generating at least one control signal has the advantage that it is possible to process the input signal and/or to generate the control signal as predefined, for example, by a control program executed by the control unit.

Based on such a processing, the respective actuating devices of a support arm system with a plurality of articulated connections can be actuated, for example, in groups in another embodiment of the method. It is thus possible, for example, to release the locking of all articulated connections of the support arm system at the same time. In a corresponding method, the control unit generates a plurality of control signals for a plurality of circuit components upon precisely one input signal of precisely one operating element, and each circuit component of the plurality of circuit components activates the respective actuating device of one of a plurality of articulated connections of the support arm system, especially the active drive of the respective actuating device. A support arm system that has, for example, a control unit with a control program executed by it as a means for carrying out such a method, may have a plurality of operating elements and individual operating elements among them by means of which the locking of precisely one articulated connection can be released, as well as an operating element by means of which the locking of all articulated connections can be released and/or one or more operating elements by means of which the locking of a respective group of articulated connections can be released.

Thus, the present invention is also a support arm system with means for carrying out the method being described here and hereinafter for operating a support arm system. For example, a control unit with a memory, with a computer program loaded into the memory and acting as a control program as well as with a processing unit in the form of or in the manner of a microprocessor for executing the control program act as means for carrying out the method.

On the whole, the present invention is also a medical device with a support arm system of the type here and hereinafter described. A medical device with such a support arm system benefits from the above-described advantages and may comprise, for example, one or more operating elements for releasing the locking, so that the operation of the support arm system and the operation of the medical device are combined at one location.

An exemplary embodiment of the present invention will be explained in more detail below on the basis of the drawings. Objects or elements corresponding to one another are designated by the same reference numbers in all figures.

The exemplary embodiment shall not be construed as a limitation of the present invention. Rather, changes and modifications are possible within the framework of the present disclosure, especially such variants and combinations which the person skilled in the art can find with respect to accomplishing the object, for example, by combining or varying individual features described in the general or special part of the specification and contained in the claims and/or in the drawings and which variants and combinations lead to a new object through combined features. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
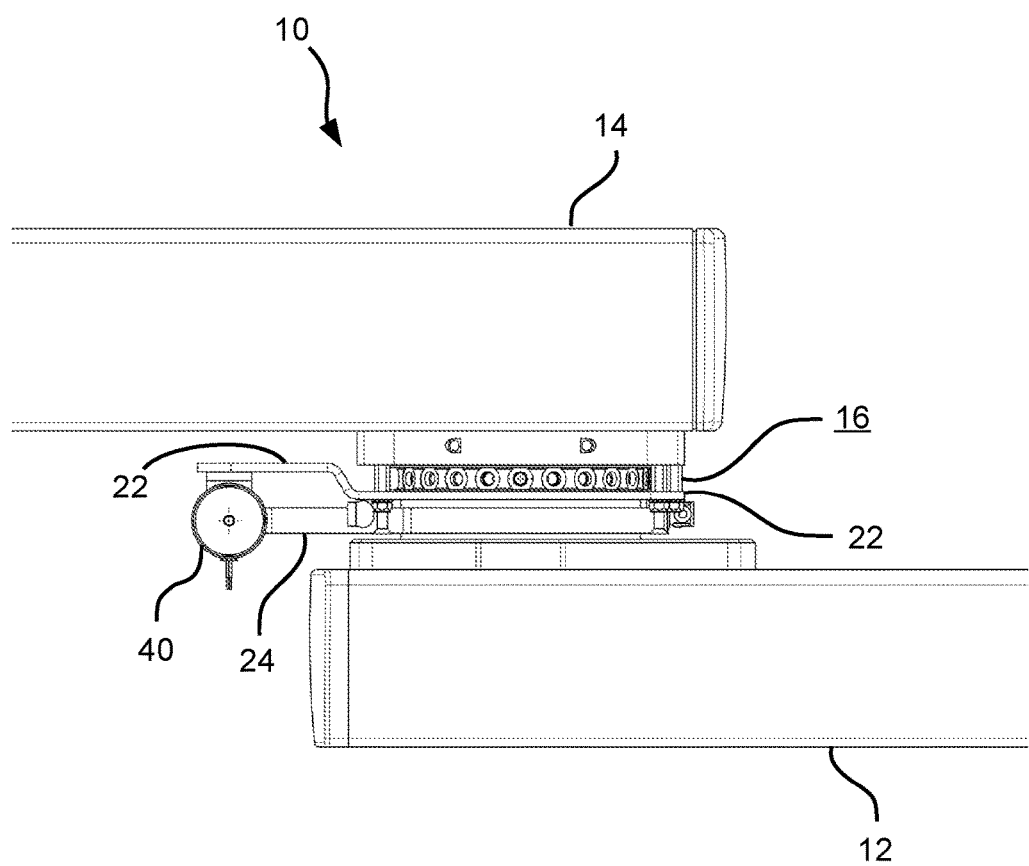
FIG. 1 is a detail side view of a support arm system.

Referring to the drawings the view in FIG. 1 shows a detail of a support arm system 10 in a schematically simplified manner. The view shows an extension arm 12 fixed, for example, on a building wall and an arm segment 14 connected to the extension arm 12 in an articulated manner. A hinge 16 (articulated connection 16) located for this purpose between the extension arm 12 and the arm segment 14 allows a rotary motion of the arm segment 14 relative to the arm 12 in a horizontal plane. The detail of the support arm system 10 shown in FIG. 1 otherwise also corresponds to the conditions between two arm segments 14. The component designated as the extension arm 12 is in this case itself a rotarily movable arm segment 14.

The support arm system 10 may accordingly have one or more arm segments 14 depending on the embodiment or the particular application. Based on a fixed basic segment, for example, an extension arm 12 acting as a basic segment and arranged at a building wall horizontally or essentially horizontally, a kinematic chain is obtained along the arm segment or each arm segment 14 directly or indirectly connected to the arm segments, and a medical device or laboratory device 70 or another device, which can be freely positioned in the room by means of the support arm system 10 by means of the support arm system 10 in the usual manner, is located at the end of the kinematic chain, i.e., at the free end of the "last" arm segment 14.

Details of the hinge 16, by means of which the rotary movability of the arm segment 14 relative to an extension arm 12, a support or the like, which is located in front of it or relative to an arm segment 14 located in front of it, is achieved, will be discussed below only to the extent to which this is significant in connection with the lockability of the hinge 16, which lockability is in the foreground here. Possibilities of embodiment for embodying the hinge 16 are known in the state of the art. Reference can thus be made to the support arm system according to US 2011/303499 A1 mentioned in the introduction or to the current support arm systems of the applicant and to the hinges used there (US 2011/303499 A1 is incorporated herein by reference in its entirety).

Figure 2:
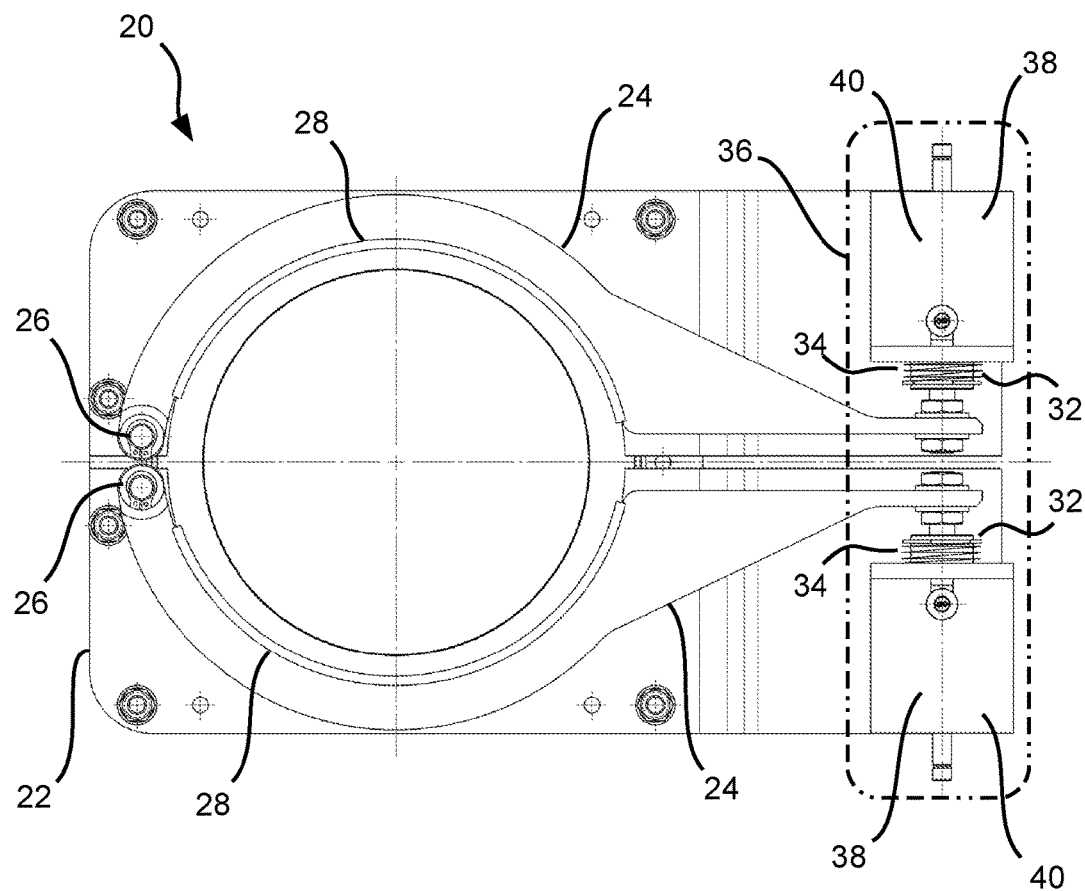
FIG. 2 is a locking device for an articulated connection of the support arm system according to FIG. 1.

The view in FIG. 2 shows an embodiment of a device for locking an articulated connection 16 in a support arm system 10 of the type shown in FIG. 1, which device is also called locking device 20. The locking device 20 comprises a carrier 22 acting as a mounting platform. Two pivotingly movable brake shoe levers 24 are arranged on the carrier 22 in the embodiment shown. The pivoting movability is brought about in the embodiment shown by means of two bearing bolts 26 extending upright on the carrier 22, which define each a pivot axis for the brake shoe levers 24. The brake shoe levers 24 have brake linings 28 on inner surfaces facing each other in the manner known per se.

To lock the articulated connection 16, the brake shoe levers 24 are moved such that their brake linings 28 come into contact with a section of an outer surface of a pipe acting as an axis 30 (FIG. 3) of the hinge 16. At least one spring element 32 is provided for such a movement. Two spring elements 32 in the form of compression springs 34, which act on one of the brake shoe levers 24 each, are shown in the embodiment being shown. As an alternative, at least one tension spring acting at least indirectly on both brake shoe levers 24 may also be considered for use as a spring element 32. The spring element 32, or each spring element 32 acting as a passive drive 32, is intended to press the brake linings 28 of the brake shoe levers 24 onto the outer surface of the axis 30 and to lock the articulated connection 16 in this manner. The passive drive 32, especially the spring element 32 or each spring element 32 acting as a passive drive 32 thus applies within the locking device 20 a force, which will hereinafter be called holding force, to the brake shoe levers 24. The holding force acts in a plane extending at right angles to the longitudinal axis of the axis 30, i.e., in a plane extending at right angles to the axis of rotation of the respective arm segment 14. The articulated connection 16 is always locked without an additional force, which eliminates the locking function of the brake shoe levers 24. To eliminate the locking, an actuating device 36, which is comprised by the locking device 20 and which comprises at least one actuator 38 acting as an active drive 38, is provided. The distinction between the spring element 32 or each spring element acting as a passive drive 32, for example, two compression springs 34 or a tension spring, and the at least one actuator 38 acing as an active drive 38 shall emphasize the fact that the passive drive 32 is also effective without external signal and energy supply, so that locking of the articulated connection 16 is automatically obtained in case of failure of the power supply.

An actuator 38 each in the form of an electromagnet 40 is associated with each brake shoe lever 24 as an active drive 38 in the exemplary embodiment shown. In particular, a first actuator 38 is associated with a first brake shoe lever 24 and a second actuator 38 is associated with a second brake shoe lever 24. In case of activation of the electromagnets 40 acting as actuators 38, the brake shoe levers 24 are pivoted against the holding force, especially the spring force of the spring elements 32 (first and second spring elements), namely, they are pivoted such that the brake linings 28 are lifted off from the outer surface of the axis 30, so that the previously existing locking of the articulated connection 16 is eliminated. The actuator 38 or each actuator 38 consequently exerts a force counteracting the holding force within the locking device 20 on the brake shoe levers 24. This counteracting force is called releasing force for distinction. The releasing force acts in the same plane as the holding force, i.e., in a plane extending at right angles to the axis of rotation of the respective arm segment 14. As soon as the activation of the actuators 38 ends by means of a corresponding control signal 50 (FIG. 5) and the releasing force does not act any longer, the brake shoe levers 24 are again pressed onto the outer surface of the axis 30 based on the holding force, i.e., especially under the effect of the spring force of the spring elements 32, and the articulated connection 16 is locked again.

The actuation of the actuators 38 consequently takes place whenever an arm segment 14 shall be pivoted. When a respective desired target position of the arm segment 14 is reached subsequent to the pivoting, the activation of the actuators 38 is again ended and the previously movable articulated connection 16 is locked again.

Figure 3:
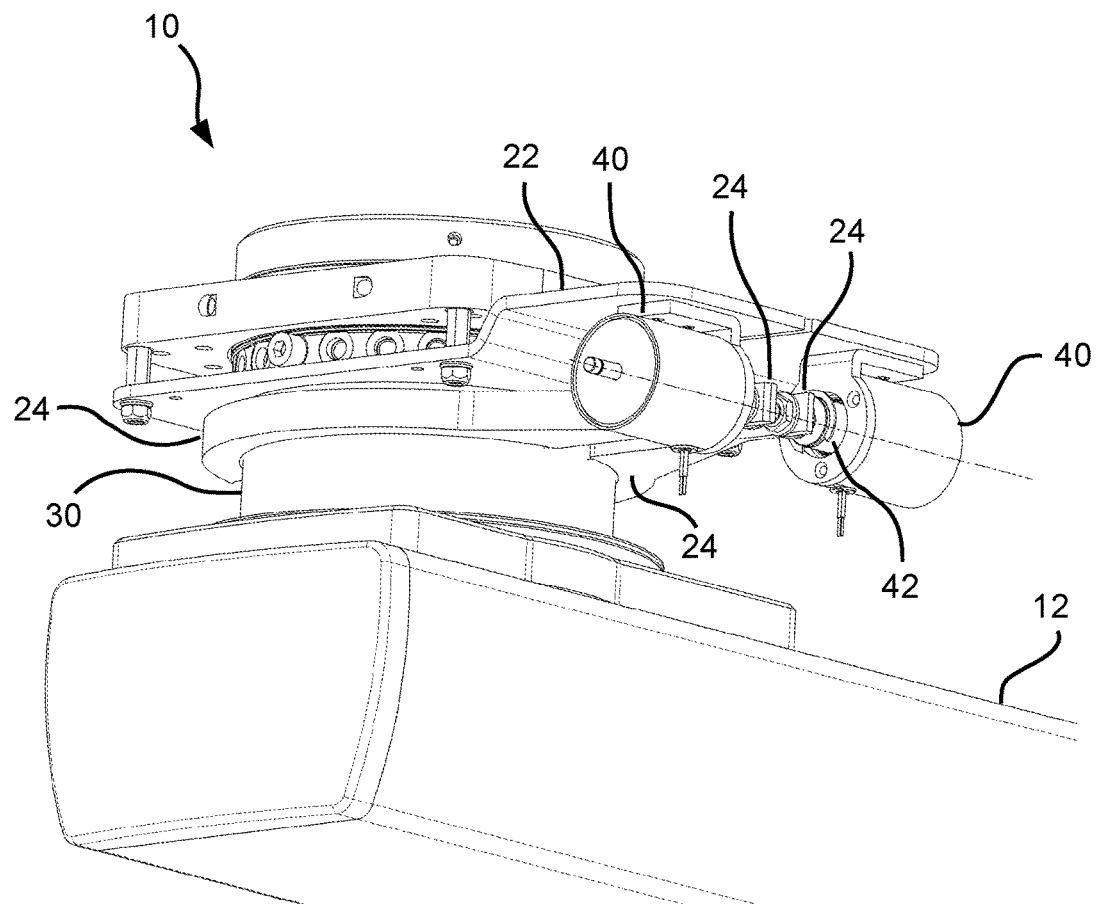
FIG. 3 is a detail perspective view of the support arm system.

The view in FIG. 3 shows the detail of the support arm system 10 from FIG. 1 in a perspective view and without the arm segment 14. The pipe acting as an axis 30 and defining the axis of rotation of the hinge 16 and of the adjoining arm segment 14 can be seen in this view. It can be seen based on the position of the carrier 22 that the arm segment 14, not shown, is at right angles to the extension arm 12 in this configuration.

Figure 4:
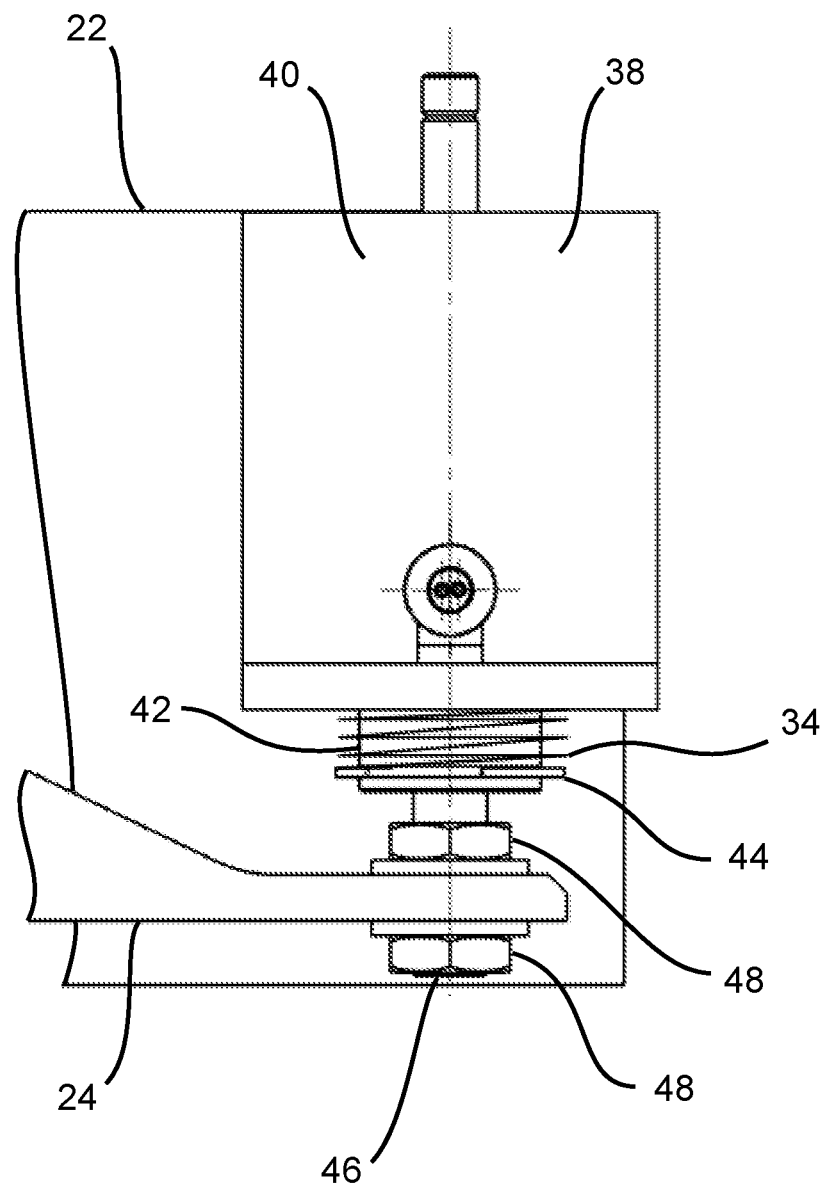
FIG. 4 is an enlarged detail view of the locking device shown in FIG. 2.

The further description is continued with reference to the view in FIG. 4. This shows an enlarged detail of the view in FIG. 2, namely, one of the two electromagnets 40 and the end of the brake shoe lever 24, on which this acts. It can be better seen there than in the view shown in FIG. 2 that the compression spring 34 in the embodiment shown as an example surrounds in some sections a core 42 of the electromagnet 40, which core is movable relative to a coil of the electromagnet 40. The core 42 is axially movable, in principle, in a manner known per se in the interior of the cylindrical coil of the electromagnet 40, which coil is not shown separately, and, as this is indicated in the view shown in FIG. 4, a center line of the core 42 coincides or essentially coincides with a center line of the coil of the electromagnet 40. The core 42 and the cylinder jacket-shaped coil are arranged coaxially or essentially coaxially.

When the electromagnet 40 is energized, the core 42 is axially displaced relative to the stationary coil. The compression spring 34 surrounds the core 42 coaxially and is in contact on one side with an end face of the electromagnet 40 (on an end face of the coil thereof). A washer 44 arranged at the core 42 acts as an opposite abutment in the exemplary embodiment shown. The core 42 ends in a threaded rod section 46, to which the free end of the brake shoe lever 24 is attached by means of a fitting hole. Two fixing elements screwed onto the threaded rod section 46, here two nuts 48 screwed onto the threaded rod section 46, enclose this rod section 46, together with a respective washer in the exemplary embodiment being shown, on both sides. The electromagnet 40 acting as an active drive 38 acts directly on the brake shoe lever 24 with this connection of the core 42 to the brake shoe lever 24. In the non-energized state of the electromagnet 40, the core 42 of said electromagnet is displaced by means of the spring force of the compression spring 34 relative to the coil of the electromagnet 40 and the brake shoe lever 24 is pivoted with this to the extent that the brake lining 28 will come into contact with the outer surface of the axis 30 and is pressed onto this. The respective articulated connection is locked by means of the resulting braking effect.

The core 42 is pulled against the spring force of the compression sprig 34 into the interior of the coil of the electromagnet 40 in the energized state, so that pivoting of the brake shoe lever 24 and, with the pivoting, a lifting off of the brake lining 28 from the outer surface of the axis 30 will result. Based on the fact that the braking effect is eliminated with the separation of the brake lining 28 from the outer surface of the axis 30, the articulated connection 16 is again freely movable.

As is shown, the locking device 20 may have two individually pivotingly movable brake shoe levers 24, a spring element 32 associated with each brake shoe lever 24 in the form of a compression spring 34 and an actuator 38 associated with each brake shoe lever 24. A locking device 20 which has only one pivotingly movable brake shoe lever 24 instead of two brake shoe levers 24 and correspondingly one spring element 32 associated herewith in the form of a compression spring 34 as well as an actuator 38 associated with the brake shoe lever 24 is also considered for use as an alternative. The configuration of the locking device 20 with a compression sprig 34 as a spring element 32 makes possible, unlike, for example, a tension spring acting on two brake shoe levers 24 arranged mutually opposite each other, both an arrangement of the brake shoe lever 24, spring element 32 and actuator 38 in pairs and an arrangement of these components as single components. The combination in space of the spring element 32 and the actuator 38, which is given in the embodiment being shown, and the effect of the respective holding or releasing force applied along a common axis (the axis is shown in the view shown in FIG. 3) guarantees, moreover, an extremely compact configuration compared to a solution in which the compression spring 34 is placed, to describe it briefly, next to the electromagnet 40 in a configuration fixed on one side and acting on the brake shoe lever 24 on the opposite side. All components of the passive and active drives 32, 38 are concentrated along a common axis of action. The action of the respective holding or releasing force applied along a common axis of action is a special form of the more general solution being proposed here, according to which the active drive 38 acts in the same plane as the passive drive 32.

The view in FIG. 1 already shows an embodiment of the actuating device 36 with electromagnets 40 as actuators 38 (recognizable from the cylindrical shape). These are arranged at the arm segment 14, which is movable by means of the articulated connection 16. The flat shape of the locking device 20 with the actuating device 36 comprised thereby, which shape is possible based on the action of the holding force and of the releasing force in the same plane, can be seen. The actuating device 36, in particular, may be surrounded by a housing, not shown here, in case of arrangement at the arm segment 14.

Figure 5:
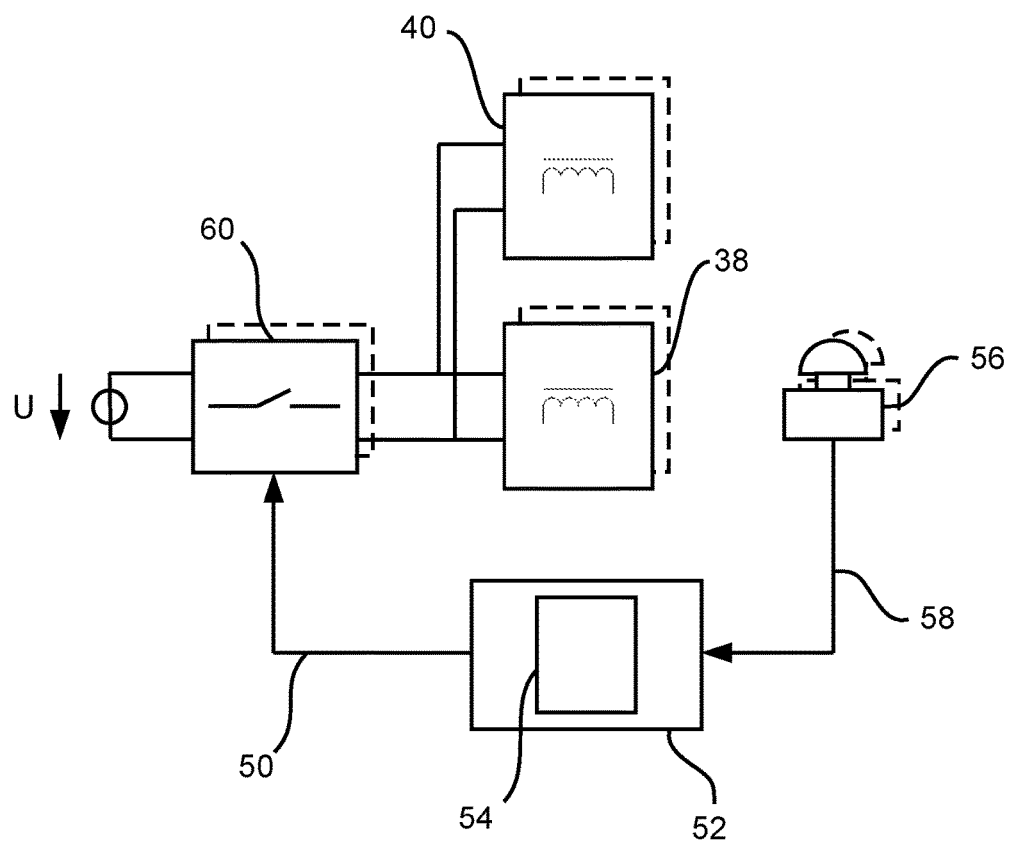
FIG. 5 is a block diagram to illustrate a control of a support arm system according to FIG. 1 through FIG. 4.
Figure 6:
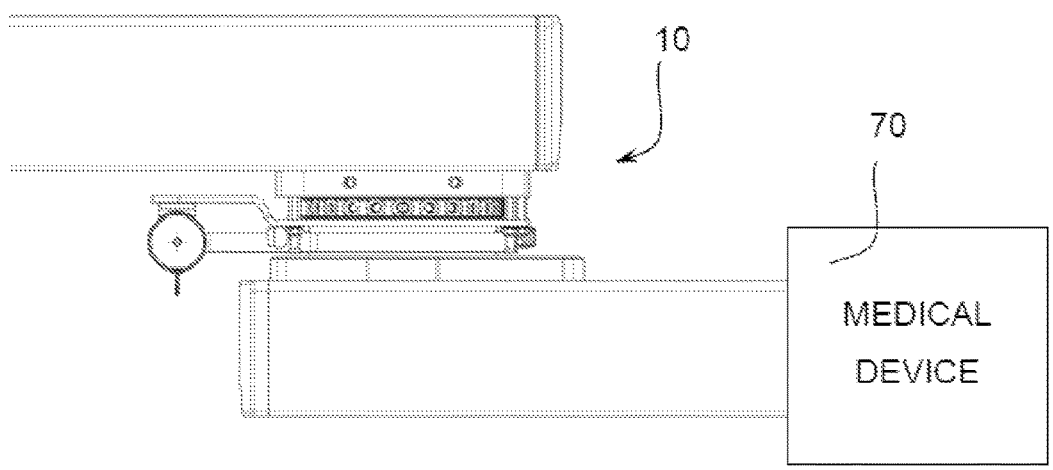
FIG. 6 is a detail side view of a support arm system connected to a medical device, which is schematically shown.

FIG. 5 shows a schematically simplified view to illustrate the actuation of the actuators 38 in an articulated connection 16 and optionally additional actuators 38 or one or more additional articulated connections 16 between additional arm segments 14. The actuator 38 or each actuator 38 is actuated by means of a control unit 52. The function of the control unit 52 is determined, for example, by a control program 54 implemented in software. The control program 54 is loaded into a memory of the control unit 52 and is executed during the operation by a processing unit in the form of or in the manner of a microprocessor. Instead of a control program 54 implemented in software or firmware with a processing unit necessary for executing same, implementation in the form of an ASIC, FPGA or the like is also possible.

During the operation of the support arm system 10, the control unit 52 processes at least one input signal 58, which can be obtained from at least one operating element 56. By actuating the operating element 56, a user of the support arm system 10 indicates the intent to which to change the position of at least one arm segment 14. The control unit 52 correspondingly generates a control signal 50 under the control of the control program 54 upon receipt of such an input signal 58. The control signal 50 acts on an electrically or electronically actuatable circuit component 60, which is shown in the view only symbolically. The activation of this circuit component brings about, for example, a through switching of a voltage supply unit to one or more actuators 38. In case of one or more electromagnets 40 acting as an actuator 38 each (likewise shown only symbolically in the view), the voltage over the coil comprised by it brings about the development of a magnetic field in a manner known per se, and the magnetic field brings about the deflection of a respective brake shoe lever 24 and hence the release of the locking of a respective articulated connection 16 of the support arm system 10.

As this is indicated as an example in the view shown in FIG. 5, provisions may be made for two actuators 38 belonging to an articulated connection 16 to be connected together in pairs such that an activation of an individual circuit component 60 brings about the simultaneous activation of respective actuators 38 that belong together in pairs.

Provisions may be made in one embodiment of the support arm system 10 for precisely two actuators 38 each to be able to be activated by means of an individual operating element 56, so that the locking of precisely one articulated connection 16 can be temporarily eliminated by means of the respective operating element 56. A corresponding plurality of operating elements 56 are accordingly provided in a support arm system 10 with a plurality of lockable articulated connections 16, so that the control unit 52 processes a corresponding plurality of input signals 58 and generates upon one respective input signal 58 a control signal 50 for activating the respective actuators 38, especially two actuators 38 each, which are connected together in pairs and belong to the same articulated connection 16. The locking of each articulated connection 16 can then be released individually and re-established when a respective desired target position is reached. As an alternative, a plurality of control signals 50 may also be generated in a support arm system 10 with a plurality of lockable articulated connections 16 by means of precisely one operating element 56 and based on an input signal 58 which can be obtained from said operating element by means of the control unit 52 and under the control of the control program 54, so that locking of a plurality of articulated connections 16 or of all the articulated connections 16 comprised by the support arm system 10 can be released simultaneously and re-established when a desired target position of the support arm system 10 is reached. Provisions may be made in a special embodiment of the support arm system 10 for the support arm system to comprise one or more operating elements 56 for releasing the locking of precisely one respective articulated connection 16 and one or more operating elements 56 for simultaneously releasing a plurality of or all articulated connections 16 of the support arm system 10. The above explanations correspondingly apply to articulated connections 16 in which only one brake lever 24 is provided for locking, so that the actuation of one actuator 38 each is sufficient for releasing the locking.

Individual essential aspects of the description presented here can finally be briefly summarized as follows: A support arm system 10 as well as a method for operating same are described, wherein the support arm system 10 comprises at least one lockable articulated connection 16, a locking device 20 associated with the articulated connection 16 with a passive drive 32 as well as an actuating device 36 associated with the locking device 20 with an active drive 38, and wherein the active drive 38 acts in the same plane as the passive drive 32.

While specific embodiments of the invention have been shown and described in detail to illustrate the application of the principles of the invention, it will be understood that the invention may be embodied otherwise without departing from such principles.

APPENDIX

List of Reference Numbers

10 Support arm system
12 Extension arm
14 Arm segment
16 Hinge/articulated connection
18 (blank)
20 Locking device
22 Carrier
24 Brake shoe lever
26 Bearing bolt
28 Brake lining
30 Axis
32 Passive drive/spring element
34 Compression spring
36 Actuating device
38 Active drive/actuator
40 Electromagnet
42 Core
44 Washer
46 Threaded rod section
48 Nut
50 Control signal
52 Control unit
54 Control program
56 Operating element
58 Input signal
60 Circuit component
70 Medical device

What is claimed is:

1. A support arm system comprising at least one lockable articulated connection with a pivot axis, the articulated connection comprising a locking device associated with the articulated connection, the locking device comprising:
   at least one brake shoe lever applying a braking force at the articulated connection, the braking force being applied perpendicular to the pivot axis;
   a passive drive, passively applying a passive drive force on the at least one brake shoe lever; and
   an actuating device associated with the locking device, the actuating device comprising an active drive applying an active drive force relative to the passive drive force, upon being actuated, wherein the active drive force acts in a same plane as the passive drive force and the braking force is applied in said same plane or in a plane which is parallel to said same plane and closely adjacent to said same plane.

2. A support arm system in accordance with claim 1, wherein the active drive is directly connected to the at least one brake shoe lever, to apply the counter drive force directly from the active drive to the at least one brake shoe lever.

3. A support arm system in accordance with claim 1, wherein the passive drive force and the active drive force are applied along a common axis.

4. A support arm system in accordance with claim 1, wherein:
   the active drive comprises at least one electromagnet associated with a free end of the brake shoe lever.

5. A support arm system in accordance with claim 4, wherein the passive drive comprises a compression spring concentrically surrounding a core of the electromagnet, in some sections.

6. A support arm system in accordance with claim 1, wherein:
   the passive drive comprises at least one compression spring associated with a free end of the at least one brake shoe lever.

7. A support arm system in accordance with claim 6, wherein:
   the active drive comprises at least one electromagnet associated with the free end of the at least one brake shoe lever; and
   the compression spring concentrically surrounds a core of the electromagnet, in some sections.

8. A support arm system in accordance with claim 1, wherein the locking device further comprises another brake shoe lever to provide two brake shoe levers with brake linings facing one another, wherein the active drive comprises a first active drive operatively connected to one of the two brake shoe levers and a second active drive operatively connected to another of the two brake shoe levers.

9. A medical device system comprising:
   a medical device; and
   a support arm system connected to the medical device, the support arm system comprising a first arm segment, a second arm segment and an articulated connection connecting the first arm segment to the second arm segment and having a pivot axis, the articulated connection comprising a locking device associated with the articulated connection, the locking device comprising:
   at least one brake shoe lever applying a braking force at the articulated connection, the braking force being applied perpendicular to the pivot axis;
   a passive drive, passively applying passive drive force on the at least one brake shoe lever; and
   an actuating device associated with the locking device, the actuating device comprising an active drive applying an active drive force relative to the passive drive force, upon being actuated, wherein the active drive force acts in a same plane as the passive drive force and the braking force is applied in said same plane or in a plane which is parallel to said same plane and closely adjacent to said same plane.

10. A medical device system in accordance with claim 9, wherein the active drive is directly connected to the at least one brake shoe lever.

11. A medical device system in accordance with claim 9, wherein the passive drive force and the active drive force are applied along a common axis.

12. A medical device system in accordance with claim 9, wherein:
    the active drive comprises at least one electromagnet associated with a free end of the brake shoe lever.

13. A medical device system in accordance with claim 12, wherein the passive drive comprises a compression spring concentrically surrounding a core of the electromagnet acting, in some sections.

14. A medical device system in accordance with claim 9, wherein:
    the passive drive comprises at least one compression spring associated with a free end of a brake shoe lever and the least one compression spring acts as the passive drive.

15. A medical device system in accordance with claim 14, wherein:
    the active drive comprises at least one electromagnet associated with the free end of the at least one brake shoe lever; and
    the compression spring concentrically surrounds a core of the electromagnet, in some sections.

16. A medical device system in accordance with claim 9, wherein the locking device further comprises another brake shoe lever to provide two brake shoe levers with brake linings facing one another, wherein the active drive comprises a first active drive operatively connected to one of the two brake shoe levers and a second active drive operatively connected to another of the two brake shoe levers.

17. A method for operating a support arm system comprising:
    providing the support arm system with at least one lockable articulated connection with a pivot axis, the articulated connection comprising a locking device associated with the articulated connection, the locking device comprising at least one brake shoe lever applying a braking force at the articulated connection, the braking force being applied perpendicular to the pivot axis, a passive drive, passively applying a passive drive force on the at least one brake shoe lever and an actuating device associated with the locking device, the actuating device comprising an active drive applying an active drive force relative to the passive drive force, upon being actuated, wherein the active drive force acts in a same plane as the passive drive force and the braking force is applied in said same plane or in a plane which is parallel to said same plane and closely adjacent to said same plane; and;
    providing an operating element for actuating a circuit component; and
    generating a control signal upon actuation of the operating element for actuating the circuit component wherein the active drive of the actuating device is activated by the circuit component.

18. A method in accordance with claim 17, wherein:
a control unit generates the control signal for actuating the circuit component;
an input signal is processed by the control unit, which generates the control signal, upon the input signal being generated upon an actuation of the operating element.

19. A method in accordance with claim 18, wherein the support arm system comprises a plurality of lockable articulated connections and the control unit generates a plurality of control signals for a plurality of circuit components upon an input signal of precisely one operating element and wherein each circuit component from the plurality of circuit components activates the particular active drive of the actuating device of one of a plurality of articulated connections of the support arm system.

20. A method in accordance with claim 18, wherein:
the locking device further comprises another brake shoe lever to provide two brake shoe levers with brake linings facing one another;
the active drive comprises a first active drive with an electromagnet associated with a free end of one of the two brake shoe levers and acting on one of the two brake shoe levers and a second active drive with an another electromagnet associated with a free end of another of the two brake shoe levers and acting on the other of the two brake shoe levers; and
the passive drive comprises a first compression spring associated with the free end of the one of the brake shoe levers and a second compression spring associated with the free end of the other of the brake shoe levers.

* * * * *